United States Patent [19]

Haber et al.

[11] Patent Number: 5,686,608

[45] Date of Patent: *Nov. 11, 1997

[54] PROCESS FOR CROSS-COUPLING AROMATIC BORON COMPOUNDS WITH AROMATIC HALOGEN COMPOUNDS OR PERFLUOROALKYLSULFONATES

[75] Inventors: Steffen Haber, Germersheim; Javier Manero, Frankfurt, both of Germany

[73] Assignee: Hoechst Aktiengesellschaft, Frankfurt, Germany

[*] Notice: The term of this patent shall not extend beyond the expiration date of Pat. No. 5,550,236.

[21] Appl. No.: 427,662

[22] Filed: Apr. 24, 1995

[30] Foreign Application Priority Data

Apr. 26, 1994 [DE] Germany ............... 44 14 499.7

[51] Int. Cl.$^6$ ............ C07D 213/26; C07D 239/30; C07D 401/04; C07D 403/04

[52] U.S. Cl. ........... 544/316; 544/334; 544/335; 544/333; 544/224; 544/242; 544/238; 544/229; 544/409; 544/410; 544/405; 546/286; 546/303; 546/290; 546/259; 546/345; 546/346; 546/339; 546/13; 546/14; 548/239; 548/110; 558/357; 568/642; 568/437; 570/143; 570/182; 570/190; 560/102; 564/181; 549/213; 549/214

[58] Field of Search ............ 558/357; 544/334, 544/316, 335, 315, 224, 242, 409, 410, 333, 238, 405, 229; 546/345, 286, 303, 290, 259, 346, 339; 548/239

[56] References Cited

U.S. PATENT DOCUMENTS

| | | |
|---|---|---|
| 5,162,325 | 11/1992 | Chakravarty et al. ............ 514/259 |
| 5,254,776 | 10/1993 | Lang et al. ............ 570/190 |

FOREIGN PATENT DOCUMENTS

| | | |
|---|---|---|
| 39 30 663 C1 | 9/1989 | Germany. |
| 4307243 | 10/1993 | Germany. |
| 2280181 | 1/1995 | United Kingdom. |
| WO 89/03821 | 5/1989 | WIPO. |

OTHER PUBLICATIONS

Blart, Errol et al., "Palladium (O)–Catalyzed Substitution of Allylic Substrates in an Aqueous–Organic Medium" Tetrahedron, 50, No. 2, pp. 505–514, 1994. Month of publication not provided.

Casalnuovo, Albert L., et al., "Palladium–Catalyzed Alkylations in Aqueous Media" J. Am. Chem. Soc. 112, pp. 4324–4330, 1990. Month of publication not provided.

Genet, Jean Pierre et al., "Palladium–Catalyzed Cross–Coupling Reactions in a Homogeneous Aqueous Medium" SYNLETT, Sep. 1992, pp. 715–717.

Hermann, Wolfgang et al., "Water–Soluble Ligands, Metal Complexes, and Catalysts: Synergism of Homogeneous and Heterogeneous Catalysis" Angew Chem. Int. Ed. Engl. 32, Nov. 1993, pp. 1524–1544.

*Primary Examiner*—Matthew V. Grumbling
*Assistant Examiner*—King Lit Wong
*Attorney, Agent, or Firm*—Curtis, Morris & Safford, P.C.

[57] ABSTRACT

A process for preparing polycyclic aromatic compounds by cross-coupling aromatic boron compounds with aromatic halogen compounds or perfluoroalkylsulfonates in the presence of metallic palladium as catalyst comprises adding to the reaction a) at least one water-soluble complexing ligand and b) sufficient water for the reaction mixture to form an aqueous phase.

The reaction of the invention proceeds chemoselectively so that even electrophilic groups such as esters or nitriles do not have an adverse effect on the course of the reaction.

The use according to the invention of a water-soluble complexing ligand in an aqueous phase enables polycyclic aromatic compounds to be prepared in very good yields and at the same time very high purity, in particular without contamination by the complexing ligands.

10 Claims, No Drawings

PROCESS FOR CROSS-COUPLING AROMATIC BORON COMPOUNDS WITH AROMATIC HALOGEN COMPOUNDS OR PERFLUOROALKYLSULFONATES

The invention relates to a process for preparing polycyclic aromatic compounds by cross-coupling aromatic boron compounds with aromatic halogen compounds or perfluoroalkylsulfonates with catalysis by metallic palladium.

The palladium-catalyzed cross-coupling reaction of terminal alkynes and organometallic alkyl, alkenyl, allyl or aryl compounds with alkyl, alkenyl, allyl or aryl halides or perfluoroalkylsulfonates has been utilized to an increasing extent for some years in many areas of organic synthesis (see, for example, B. M. Trost, T. R. Verhoeven in: Comprehensive Organometallic Chemistry, Volume 8, p. 779 ff., Pergamon Press, Oxford 1982).

Aromatic boron compounds, such as boronic acids and their derivatives or boranes, have also been used for coupling with aromatic halogen compounds or perfluoroalkylsulfonates (see, for example, N. Miyaura, T. Yanagi, A. Suzuki in Synthetic Communications 11 (1981) 513; EP-A 0 470 795 and EP-A 0 354 434).

The processes described therein are homogeneously catalyzed processes using Pd(O) complexes, in particular tetrakis(triphenylphosphane)palladium(O), which are soluble in organic solvents.

However, the disadvantage of these processes is clearly in the high catalyst costs which make economic transfer of the processes to a relatively large production scale (kg, t) difficult. Furthermore, the homogeneous reaction procedure makes efficient regeneration of the palladium catalyst difficult and can easily lead to palladium contamination of both the products formed in the reaction and the waste.

It is also known that water-soluble palladium complexes can be used for the abovementioned coupling reactions and that the reactions can be carried out in purely aqueous or two-phase systems comprising an organic and a water phase (see, for example, U.S. Pat. No. 5,043,510; A. L. Casalnuovo and J. C. Calabrese, J. Am. Chem. Soc. 112 (1990) 4324 and J. P. Genet et al., Synlett 1992, 715). Use is here made of water-soluble phosphane ligands, such as trisodium triphenylphosphane-3,3',3"-trisulfonate (tppts), to obtain the water-soluble palladium complex.

However, the processes carried out purely homogeneously in the aqueous phase likewise suffer from the above-described disadvantages and, for the two-phase systems, entrainment of the palladium in the organic phase is observed.

Processes which circumvent these problems by heterogeneous use of the catalyst have therefore been developed. German Patent 39 30 663 describes a process for preparing liquid-crystalline compounds, in which halides and organometallic compounds, including boronic acids, are reacted in inert solvents using metallic palladium, if desired applied to a support material, in the presence or absence of a metal alkoxide. Although this procedure can substantially reduce the catalyst costs and the palladium can easily be regenerated after the reactions are complete, this process does not always give the desired coupling product in satisfactory yields and in sufficient purity.

It is thus an object of the present invention to find a process for coupling aromatic boron compounds with aromatic halogen compounds or perfluoroalkylsulfonates, which at least partially remedies the disadvantages described.

It has now surprisingly been found that reaction of aromatic boron compounds, such as boronic acids, with aromatic halogen compounds or perfluoroalkylsulfonates in an aqueous reaction medium in the presence of a base, catalytic amounts of metallic palladium and at least one water-soluble complexing ligand gives polycyclic aromatic compounds in excellent yields and very high purities.

The invention accordingly provides a process for preparing polycyclic aromatic compounds by cross-coupling aromatic boron compounds with aromatic halogen compounds or perfluoroalkylsulfonates in the presence of metallic palladium as catalyst, which comprises adding to the reaction a) at least one water-soluble complexing ligand and
b) sufficient water for the reaction mixture to form an aqueous phase.

The reaction of the invention proceeds chemoselectively so that even electrophilic groups such as esters or nitriles do not adversely affect the course of the reaction.

The use according to the invention of a water-soluble complexing ligand in an aqueous phase allows the preparation of polycyclic aromatic compounds in very good yields with simultaneously very high purity, in particular without contamination by the complexing ligands.

In addition, the palladium metal which is present as a solid after the reaction is complete can easily be separated off, regenerated and recycled to the catalysis process, which achieves an additional lowering of the process costs and avoids the presence of palladium in the waste products.

To carry out the process of the invention, the aromatic boron compound, the aromatic halogen compound or the perfluoroalkylsulfonate, the base, the catalytic amount of metallic palladium and the water-soluble ligand are added to water or preferably a mixture of water and one or more inert organic solvents and are stirred at a temperature of from 0° C. to 200° C., preferably at from 30° C. to 170° C., particularly preferably at from 50° C. to 150° C., most preferably at from 60° C. to 120° C., for a period of from 1 hour to 100 hours, preferably from 5 hours to 70 hours, particularly preferably from 5 hours to 50 hours. After the reaction is complete, the Pd catalyst which is obtained as a solid is separated off, for example, by filtration and the crude product is freed of the solvent or solvents. In the case of products which are not completely water-soluble, the ligand is completely separated off in the separation of the water phase from the crude product. Further purification can subsequently be carried out by methods known to those skilled in the art and matched to the respective product, for example by recrystallization, distillation, sublimation, zone melting, melt crystallization or chromatography.

The process of the invention can be carried out in a two-phase system comprising an aqueous phase and a solid phase, i.e. the catalyst. The aqueous phase can here contain a water-soluble organic solvent in addition to water.

However, preference is given to carrying out the reaction in a three-phase system comprising an aqueous phase, an organic phase and the solid catalyst phase. This applies in particular when the starting materials used or the products prepared according to the invention are not completely water-soluble.

Suitable organic solvents for the process of the invention are, for example, ethers such as diethyl ether, dimethoxymethane, diethylene glycol dimethyl ether, tetrahydrofuran, dioxane, diisopropyl ether, tert-butyl methyl ether, hydrocarbons such as hexane, iso-hexane, heptane, cyclohexane, benzene, toluene, xylene, alcohols such as methanol, ethanol, 1-propanol, 2-propanol, ethylene glycol, 1-butanol, 2-butanol, tert-butanol, ketones such as acetone, ethyl methyl ketone, iso-butyl methyl ketone, amides such as dimethylformamide, dimethylacetamide, N-methylpyrrolidone, nitriles such as acetonitrile, propionitrile, butyronitrile, and mixtures of the same.

Preferred organic solvents are ethers such as dimethoxyethane, diethylene glycol dimethyl ether, tetrahydrofuran, dioxane, diisopropyl ether, hydrocarbons such as hexane, heptane, cyclohexane, benzene, toluene, xylene, alcohols such as methanol, ethanol, 1-propanol, 2-propanol, 1-butanol, 2-butanol, tert-butanol, ethylene glycol, ketones such as ethyl methyl ketone, iso-butyl methyl ketone, amides such as dimethylformamide, dimethylacetamide, N-methylpyrrolidone, and mixtures of the same.

Particularly preferred solvents are ethers such as dimethoxyethane, tetrahydrofuran, hydrocarbons such as cyclohexane, benzene, toluene, xylene, alcohols such as ethanol, 1-propanol, 2-propanol, 1-butanol, tert-butanol and mixtures of the same.

In a particularly preferred variant of the process of the invention, water, one or more solvents insoluble in water and one or more solvents soluble in water are used. Examples are mixtures of water, toluene and ethanol, water, toluene and tetrahydrofuran and water, toluene and acetonitrile, in each case preferably in a volume ratio of 1:2:1.

Bases which are preferably used in the process of the invention are alkali metal and alkaline earth metal hydroxides, alkali metal and alkaline earth metal carbonates, alkali metal hydrogen carbonates, alkali metal and alkaline earth metal acetates, alkali metal and alkaline earth metal alkoxides, and also primary, secondary and tertiary amines.

Particular preference is given to alkali metal and alkaline earth metal hydroxides, alkali metal and alkaline earth metal carbonates and alkali metal hydrogen carbonates. Most preferred are alkali metal hydroxides such as sodium hydroxide and potassium hydroxide, and also alkali metal carbonates and alkali metal hydrogen carbonates such as lithium carbonate, sodium carbonate and potassium carbonate.

In the process of the invention, the base is preferably used in a proportion of from 100 to 1000 mol %, particularly preferably from 100 to 500 mol %, very particularly preferably from 150 to 400 mol %, most preferably from 180 to 250 mol %, based on the aromatic boron compound.

The catalyst used is palladium in metallic form, hereinafter referred to only as palladium, preferably palladium in pulverized form or on a support material, e.g. palladium on activated carbon, palladium on aluminum oxide, palladium on barium carbonate, palladium on barium sulfate, palladium on aluminum silicates such as montmorillonite, palladium on $SiO_2$ and palladium on calcium carbonate, in each case having a palladium content of from 0.5 to 10% by weight. Particularly preferred are palladium in pulverized form, palladium on activated carbon, palladium on barium and/or calcium carbonate and palladium on barium sulfate, in each case having a palladium content of from 0.5 to 10% by weight. Most preferred is palladium on activated carbon having a palladium content of 5 or 10% by weight. It is also possible to use catalysts which contain, besides palladium and the support material, further dopants such as lead (Lindlar catalyst).

In the process of the invention, the palladium catalyst is used in a proportion of from 0.01 to 10 mol %, preferably from 0.05 to 5 mol %, particularly preferably from 0.1 to 3 mol %, most preferably from 0.1 to 1.5 mol %, based on the aromatic halogen compound or the perfluoroalkylsulfonate.

Water-soluble ligands suitable for the process of the invention contain, for example, sulfonic acid salt and/or sulfonic acid radicals and/or carboxylic acid salt and/or carboxylic acid radicals and/or phosphonic acid salt and/or phosphonic acid radicals and/or phosphonium groups and/or peralkylammonium groups and/or hydroxy groups and/or polyether groups having a suitable chain length.

Preferred classes of water-soluble ligands are the following types of compound substituted by the above groups: phosphanes such as trialkylphosphanes, tricycloalkylphosphanes, triarylphosphanes, dialkylarylphosphanes, alkyldiarylphosphanes and heteroarylphosphanes such as tripyridylphosphane and trifurylphosphane, with the three substituents on the phosphorus being able to be identical or different, chiral or achiral and with one or more of the ligands being able to link the phosphorus groups of a plurality of phosphanes and with a part of this link also being able to be one or more metal atoms, phosphites, phosphinous esters and phosphonous esters, phosphols, dibenzophosphols and cyclic or oligocyclic and polycyclic compounds containing phosphorus atoms.

Further suitable groups of water-soluble complexing ligands comprise, for example, bipyridines, phenanthrolines, porphyrins and alizarins which are modified with the above-mentioned groups.

Water-soluble phosphanes which are preferably used are those of the formulae (I) to (VII)

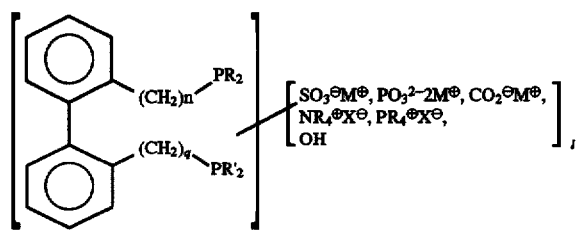

(I)

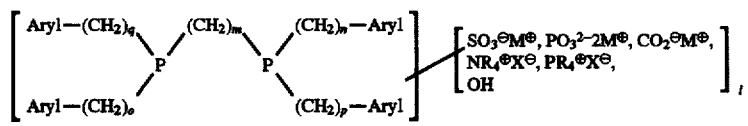

(II)

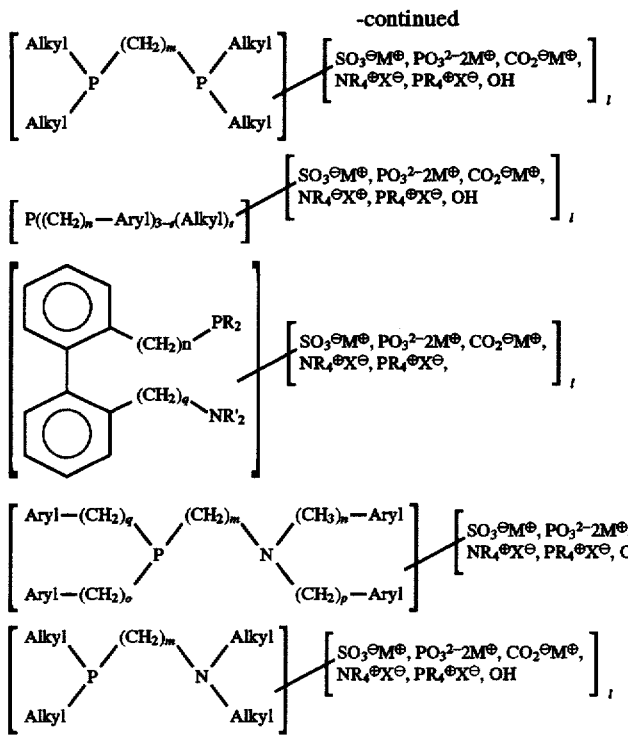

where the symbols and indices have the following meanings:

Aryl: a phenyl or naphthyl group which can also bear one or more substituents R;

Alkyl: a straight-chain or branched alkyl group having from 1 to 8 carbon atoms;

R,R': alkyl, aryl or aralkyl having from 1 to 18 carbon atoms;

M: alkali metal, alkaline earth metal or $NR_4$;

X: halogen, $BF_4$, $OSO_2CF_3$, ½[$SO_4$];

l,m: from 1 to 8;

n,o,p,q: 0, 1 to 8;

s: 0, 1 to 3.

Examples of particularly preferred water-soluble complexing ligands are shown below: (unless otherwise indicated, R has the meanings given for the formulae (I) to (VII))

1. Sulfonated phosphanes

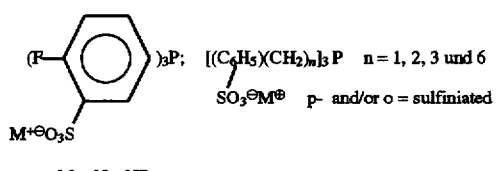

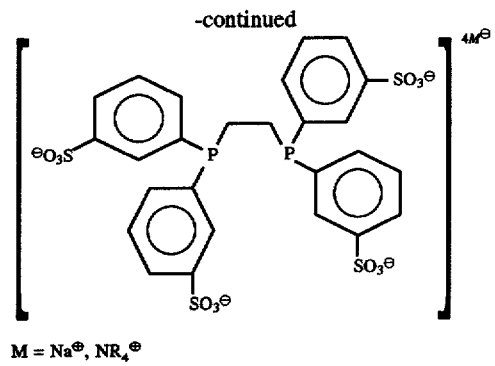

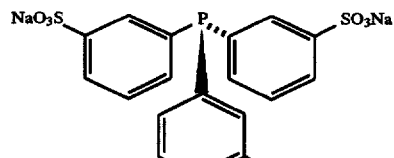

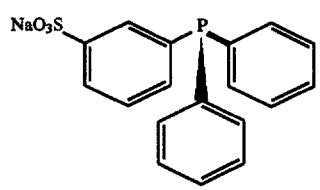

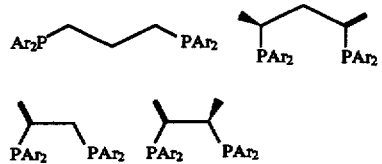

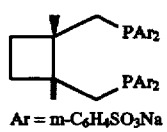
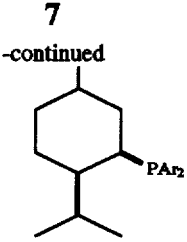

Ar = m-C₆H₄SO₃Na

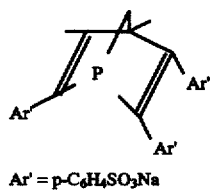

Ar' = p-C₆H₄SO₃Na

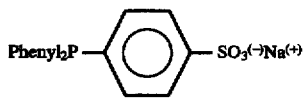

R₃₋ₙP(p-C₆H₄SO₃K)ₙ, R=C₆H₅, 2-pyridyl, 3-pyridyl; n=1-3 P[p-OC₆H₄SO₃(NH(i-octyl)₃]₃

1.1 Phosphanes having hydrophilic groups in the periphery

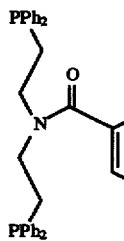
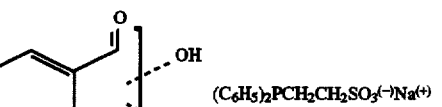

(C₆H₅)₂PCH₂CH₂SO₃(-)Na(+)

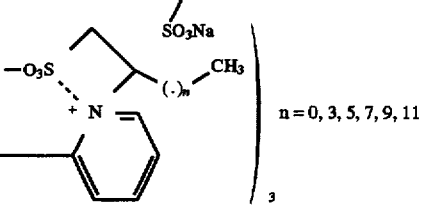

n = 0, 3, 5, 7, 9, 11

2. Phosphanes having quaternized aminoalkyl and aminoaryl substituents

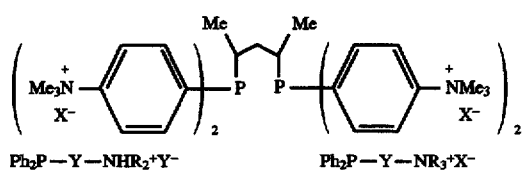

Ph₂P—Y—NHR₂⁺Y⁻    Ph₂P—Y—NR₃⁺X⁻

Y=—CH₂CH₂—, —CH(CH₃)CH₂—, —CH₂CH(CH₃)CH₂—;
R=CH₃; X=I⁻, Bu⁻, Cl⁻, OSO₂CF₃⁻, BF₄⁻

3. Carboxylated phosphanes

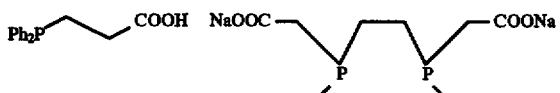
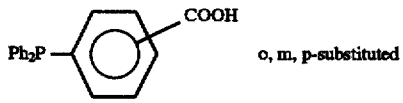

o, m, p-substituted

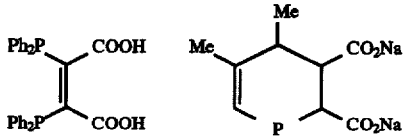
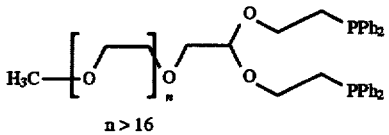

4. Phosphates having hydroxyalkyl or polyether substituents

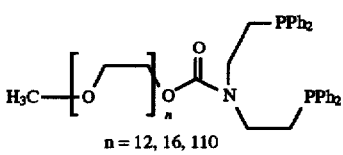

n > 16

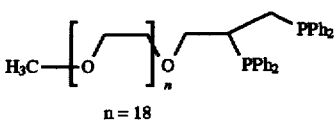

n = 12, 16, 110

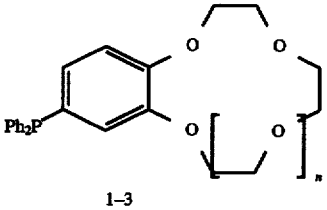

n = 18

1-3

5. Phosphinoalkylphosphonium salts

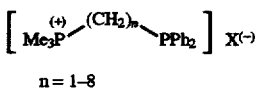

n = 1-8

X = Halogen, OSO₂CF₃⁻
BF₄⁻

6. Phosphites

P[—OC₆H₄SO₃{NH(i-octyl)₃}]₃

Most preferred water-soluble phosphine ligands are:

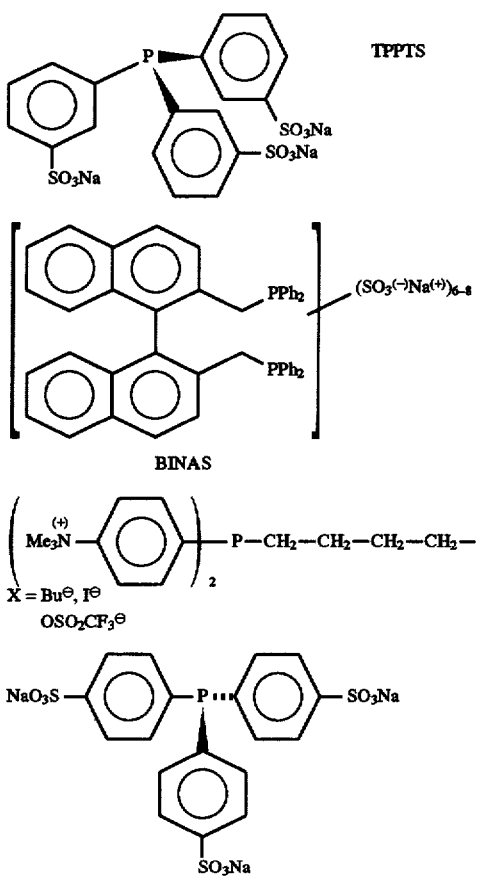

In the process of the invention, the water-soluble ligand is used in a proportion of from 0.01 to 20 mol %, preferably from 0.05 to 15 mol %, particularly preferably from 0.05 to 10 mol %, most preferably from 0.1 to 6 mol %, based on the aromatic halogen compound or the perfluoroalkylsulfonate. If desired, it is also possible to use mixtures of two or more different water-soluble ligands. The water-soluble complexing ligands to be used according to the invention are largely known from the literature. The syntheses are described, for example, in W. A. Herrmann and C. W. Kohlpainter, Angew. Chem. Int. Ed. Engl. 32 (1993) 1524 and the literature cited therein or can be carried out by methods known in the literature and familiar to those skilled in the art. The preparation of BINAS is described, for example, in the German Patent Application P 42 44 274.

Starting compounds for the process of the invention are, on the one hand, aromatic boron compounds of the formula (VIII)

Aryl—$BQ_1Q_2$ (VIII)

where

Aryl is an aromatic radical and $Q_1$, $Q_2$ are identical or different and are each —OH, $C_1$–$C_4$-alkoxy, $C_1$–$C_4$-alkyl, phenyl which can be unsubstituted or substituted by $C_1$–$C_4$-alkyl, $C_1$–$C_4$-alkoxy or halogen, or halogen or $Q_1$ and $Q_2$ together form a $C_1$–$C_4$-alkylenedioxy group, a methylene group which can be unsubstituted or substituted by one or two $C_1$–$C_4$-alkyl groups, or $Q_1$ and $Q_2$ and the boron atom are together part of a boroxine ring of the formula (IX):

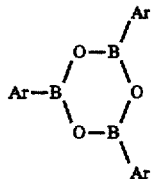

(IX)

Preference is given to aromatic boron compounds of the formula (X)

$R^1(-A^1)_k(-M^1)_l-A^2-B\ Q_1Q_2$ (X)

where $R^1$, $A^1$, $A^2$, $M^1$, $Q_1$, $Q_2$, k and l have the following meanings:

$R^1$ is benzyloxy, H, F, Cl, Br, —NC, —CN, —$CF_3$, —$OCF_3$ or a straight-chain or branched (with or without an asymmetric carbon atom) alkyl radical having from 1 to 18 carbon atoms, with one or two non-adjacent —$CH_2$— groups also being able to be replaced by —O—, —S—, —CO—, —CO—O—, —O—CO—, —CO—S—, —S—CO—, —O—CO—O—, —CH=CH—, —C≡C—, —$SO_2$—, —CON(H, $C_1$–$C_8$-alkyl)—,

or —Si($CH_3$)$_2$—, and with one or more hydrogen atoms of the alkyl radical also being able to be replaced by F, Cl, Br or CN;

$A^1$ is 1,4-phenylene, pyrazine-2,5-diyl, pyridazine-3,6-diyl, pyridine-2,5-diyl, pyrimidine-2,5-diyl, trans-1,4-cyclohexylene, naphthalene-2,6-diyl, with one or more hydrogen atoms being able to be replaced by identical or different substituents L, with L having the meanings given for $R^1$ or being 4,4-dimethylisoxazoline, and with one or two non-adjacent $CH_2$ groups of the cyclohexylene being able to be replaced by —O— or —S—, or is 1,3,4-thiadiazole-2,5-diyl, 1,3-thiazole-2,4-diyl, 1,3-thiazole-2,5-diyl, thiophene-2,4-diyl, thiophene-2,5-diyl, piperazine-1,4-diyl, piperazine-2,5-diyl, piperidine-1,4-diyl, bicyclo[2.2.2]octane-1,4-diyl, 1,3-dioxaborinane-2,5-diyl or trans-decalin-2,6-diyl;

$A^2$ is 1,4-phenylene, pyrazine-2,5-diyl, pyridazine-3,6-diyl, pyridine-2,5-diyl, pyrimidine-2,5-diyl, naphthalene-2,6-diyl, with one or more hydrogen atoms being able to be replaced by identical or different substituents L, with L having the meanings given for $R^1$ or being 4,4-dimethylisoxazoline, or is 1,3,4-thiadiazole-2,5-diyl, 1,3-thiazole-2,4-diyl, 1,3-thiazole-2,5-diyl, thiophene-2,4-diyl or thiophene-2,5-diyl;

$M^1$ is —O—, —S—, —CO—, —CO—O—, O—CO—, —CO—S—, —S—CO—, —O—CO—O—, —CH$_2$—O—, —OCH$_2$—, —CH$_2$CH$_2$—, —CH=CH—, —C≡C—, —CH(CN)—CH$_2$—, —CH$_2$—CH(CN)—, —CH=N—, —N=CH—, —CH$_2$CH$_2$CH$_2$—O—, —OCH$_2$CH$_2$CH$_2$—, —CH$_2$CH$_2$CO—O—, —O—COCH$_2$CH$_2$—, and $Q_1, Q_2$ are identical or different and are each —OH, $C_1-C_4$-alkoxy or halogen or $Q_1$ and $Q_2$ together form a $C_1-C_4$-alkylenedioxy group or $Q_1$ and $Q_2$ and the boron atom are together part of a boroxine ring of the formula (IX):

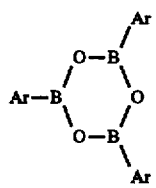

(IX)

k, l are each, independently of one another, zero or one.

$R^1$ is preferably benzyloxy, H, F, Cl, —CF$_3$, OCF$_3$, CN or a straight-chain or branched (with or without an asymmetric carbon atom) alkyl radical having from 1 to 18 carbon atoms, with one or two non-adjacent —CH$_2$— groups also being able to be replaced by —O—, —CO—, —CO—O—, —OCO—, —O—CO—O—, —CH=CH—, —C≡C—,

or —Si(CH$_3$)$_2$—, and with one or more hydrogen atoms of the alkyl radical also being able to be replaced by F, Cl or CN.

$R^1$ is particularly preferably benzyloxy, H or a straight-chain or branched (with or without an asymmetric carbon atom) alkyl radical having from 1 to 18 carbon atoms, with one or two non-adjacent —CH$_2$— groups also being able to be replaced by —O—, —CH=CH—, —C≡C—,

or —Si(CH$_3$)$_2$—.

$A^1$ is preferably 1,4-phenylene, pyrazine-2,5-diyl, pyridazine-3,6-diyl, naphthalene-2,6-diyl, pyridine-2,5-diyl, pyrimidine-2,5-diyl, with one or more hydrogen atoms being able to be replaced by identical or different substituents L, with L having the meanings given for $R^1$, or is trans-1,4-cyclohexylene in which one or two non-adjacent —CH$_2$— groups can be replaced by —O—, 1,3,4-thiadiazole-2,5-diyl or bicyclo[2.2.2]octane-1,4-diyl.

$A^1$ is particularly preferably 1,4-phenylene, 2-fluoro-1,4-phenylene, 2,3-difluoro-1,4-phenylene, 2,6-difluoro-1,4-phenylene, 2,5-difluoro-1,4-phenylene, and also pyridine-2,5-diyl, pyrimidine-2,5-diyl, with one or two hydrogen atoms being able to be replaced by identical or different substituents L, with L having the meanings given for $R^1$, or is trans-1,4-cyclohexylene.

$A^2$ is preferably 1,4-phenylene, pyrazine-2,5-diyl, pyridazine-3,6-diyl, pyridine-2,5-diyl, pyrimidine-2,5-diyl, naphthalene-2,6-diyl, with one or more hydrogen atoms being able to be replaced by identical or different substituents L, with L having the meanings given for $R^1$.

$A^2$ is particularly preferably 1,4-phenylene, 2-fluoro-1,4-phenylene, 2,3-difluoro-1,4-phenylene, 2,6-difluoro-1,4-phenylene, 2,5-difluoro-1,4-phenylene, and also pyridine-2,5-diyl, or naphthalene-2,6-diyl, with one or more hydrogen atoms being able to be replaced by identical or different substituents L, with L having the meanings given for $R^1$.

$M^1$ is preferably —O—, —CO—, —CO—O—, —O—CO—, —O—CO—O—, —CH$_2$—O—, —O—CH$_2$—, —CH$_2$—CH$_2$—, —CH=CH—, —C≡C—, —CH$_2$CH$_2$CH$_2$—O—, —O—CH$_2$CH$_2$CH$_2$—, —CH$_2$CH$_2$CO—O— or —O—CO—CH$_2$—CH$_2$—.

$M^1$ is particularly preferably —O—, —CH$_2$—O—, —O—CH$_2$—, —CH$_2$CH$_2$—, —CH=CH— or —C≡C—.

Most preferred are the aromatic boronic acids of the formulae Xa to Xh shown below:

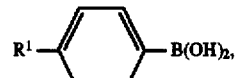

Xa

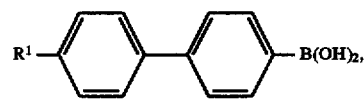

Xb

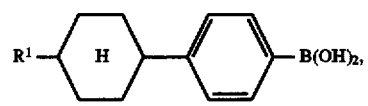

Xc

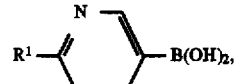

Xd

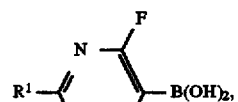

Xe

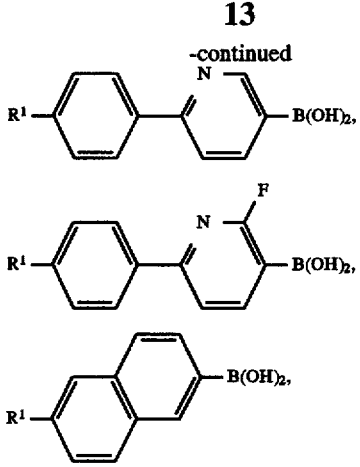

The aromatic boron compounds used are either known or can be prepared by known methods as are described, for example, in Houben Weyl Methoden der Organischen Chemie, Georg Thieme-Verlag, Stuttgart, Volume 13/3a. It is thus possible, for example, to obtain boronic acids, preferably those of the formula II, from aromatic alkali metal and magnesium compounds by reaction with trialkoxyboranes and subsequent hydrolysis.

The second class of starting compounds for the process of the invention are aromatic halogen compounds or aromatic perfluoroalkylsulfonates, preferably those of the formula XI $$X-A^3(-M^2)_m(-A^4)_n-R^2 \qquad (XI)$$

where $R^2$, $A^3$, $A^4$, $M^2$, X, m and n have the following meanings:

$R^2$ is benzyloxy, H, F, Cl, Br, —NC, —CN, —$CF_3$, —$OCF_3$, isoxazoline or a straight-chain or branched (with or without an asymmetric carbon atom) alkyl radical having from 1 to 18 carbon atoms, with one or two non-adjacent —$CH_2$— groups also being able to be replaced by —O—, —S—, —CO—, —CO—O—, —O—CO—, —CO—S—, —S—CO—, —O—CO—O—, —$SO_2$—, —CON(H, $C_1$-$C_8$-alkyl)—, —CH=CH—, —C≡C—,

or —Si(CH$_3$)$_2$—, and with one or more hydrogen atoms of the alkyl radical also being able to be replaced by F, Cl, Br or CN;

$A^4$ is 1,4-phenylene, pyrazine-2,5-diyl, pyridazine-3,6-diyl, pyridine-2,5-diyl, pyrimidine-2,5-diyl, naphthalene-2,6-diyl, trans-1,4-cyclohexylene, in which one or two non-adjacent CH$_2$ groups can be replaced by —O— or —S— and with one or more hydrogen atoms being able to be replaced by identical or different substituents L, with L having the meanings given for R$^1$ or being CHO, or 4,4-dimethylisoxazoline, or is 1,3,4-thiadiazole-2,5-diyl, 1,3-thiazole-2,4-diyl, 1,3-thiazole-2,5-diyl, thiophene-2,4-diyl, thiophene-2,5-diyl, piperazine-1,4-diyl, piperazine-2,5-diyl, piperidine-1,4-diyl, bicyclo[2.2.2]octane-1,4-diyl, 1,3-dioxaborinane-2,5-diyl or trans-decalin-2,6-diyl, $A^3$ is 1,4-phenylene, pyrazine-2,5-diyl, pyridazine-3,6-diyl, pyridine-2,5-diyl, pyrimidine-2,5-diyl, naphthalene-2,6-diyl, with one or more hydrogen atoms being able to be replaced by identical or different substituents L, with L having the meanings given for R$^1$ or being CHO, or 4,4-dimethylisoxazoline, or is 1,3,4-thiadiazole-2,5-diyl, 1,3-thiazole-2,4-diyl, 1,3-thiazole-2,5-diyl, thiophene-2,4-diyl or thiophene-2,5-diyl, $M^1$ is —O—, —S—, —CO—, —CO—O—, O—CO—, —CO—S—, —S—CO—, —O—CO—O—, —CH$_2$—O—, —OCH$_2$—, —CH$_2$CH$_2$—, —CH=CH—, —C≡C—, —CH(CN)—CH$_2$—, —CH$_2$—CH(CN)—, —CH=N—, —N=CH—, —CH$_2$CH$_2$CH$_2$—O—, —OCH$_2$CH$_2$CH$_2$—, —CH$_2$CH$_2$CO—O—, —O—COCH$_2$CH$_2$—, and X is chlorine, bromine, iodine or —OSO$_2$—C$_p$F$_{2p+1}$, where p is an integer from 1 to 10;

m, n are each, independently of one another, zero or one.

$R^2$ is preferably benzyloxy, H, F, Cl, Br, —CN, —CF$_3$, OCF$_3$ or a straight-chain or branched (with or without an asymmetric carbon atom) alkyl radical having from 1 to 18 carbon atoms, with one or two non-adjacent —CH$_2$— groups also being able to be replaced by —O—, —CO—, —CO—O—, —O—CO—, —O—CO—O—, —CH=CH—, —C≡C—,

or —Si(CH$_3$)$_2$—, and with one or more hydrogen atoms of the alkyl radical also being able to be replaced by F, Cl or CN.

$R^2$ is particularly preferably benzyloxy, H, Cl, Br or a straight-chain or branched (with or without an asymmetric carbon atom) alkyl radical having from 1 to 18 carbon atoms, with one or two non-adjacent —CH$_2$— groups also being able to be replaced by —O—, —CO—, —CO—O—, —O—, —O—CO—, —O—CO—O—, —CH=CH—, —C≡C—, or —Si(CH$_3$)—.

$A^3$ is preferably 1,4-phenylene, pyrazine-2,5-diyl, pyridazine-3,6-diyl, pyridine-2,5-diyl, pyrimidine-2,5-diyl, naphthalene-2,6-diyl, with one or more hydrogen atoms being able to be replaced by identical or different substituents L, with L having the meanings given for R$^1$ or being CHO or 4,4-dimethylisoxazoline or is 1,3,4-thiadizole-2,5-diyl.

$A^3$ is particularly preferably 1,4-phenylene, 2-fluoro-1,4-phenylene, 2,3-difluoro-1,4-phenylene, 2,6-difluoro-1,4-phenylene, 2,5-difluoro-1,4-phenylene, and also pyrazine-2,5-diyl, pyridazine-2,5-diyl, pyrimidine-2,5-diyl or naphthalene-2,6-diyl, with one or more hydrogen atoms being able to be replaced by identical or different substituents L, with L having the meanings given for R$^1$ or being CHO or 4,4-dimethylisoxazoline.

$A^4$ is preferably 1,4-phenylene, pyrazine-2,5-diyl, pyridazine-3,6-diyl, pyridine-2,5-diyl, pyrimidine-2,5-diyl, trans-1,4-cyclohexylene in which one or two non-adjacent CH$_2$ groups can be replaced by —O—, naphthalene-2,6-diyl, with one or more hydrogen atoms being able to be replaced by identical or different substituents L, with L having the meanings given for R$^1$, or is 1,3,4-thiadiazole-2,5-diyl, or bicyclo[2.2.2]octane-1,4-diyl.

$A^4$ is particularly preferably 1,4-phenylene, 2-fluoro-1,4-phenylene, 2,3-difluoro-1,4-phenylene, 2,6-difluoro-1,4- phenylene, 2,5-difluoro-1,4-phenylene, and also pyridine-2, 5-diyl, pyrimidine-2,5-diyl, trans-1,4-cyclohexylene, naphthalene-2,6-diyl, with one or more hydrogen atoms being able to be replaced by identical or different substituents L, with L having the meanings given for $R^1$.

$M^2$ is preferably —O—, —CO—, —CO—O—, —O—CO—, —O—CO—O—, —CH$_2$—O—, —O—CH$_2$—, —CH$_2$CH$_2$—, —CH=CH—, —C≡C—, —CH$_2$CH$_2$CH$_2$—O—, —O—CH$_2$CH$_2$CH$_2$—, —CH$_2$CH$_2$CO—O— or —O—CO—CH$_2$CH$_2$—.

$M^2$ is particularly preferably —O—, —CO—, —CO—O—, O—CO—, —O—CO—O—, —CH$_2$—O—, —O—CH$_2$—, —CH$_2$CH$_2$—, —CH=CH—, —C≡C—, —CH$_2$CH$_2$CH$_2$—O—, —O—CH$_2$CH$_2$CH$_2$—, —CH$_2$CH$_2$CO—O— or —O—CO—CH$_2$CH$_2$-.

X is preferably bromine, iodine or —OSO$_2$—C$_p$F$_{2p+1}$, where p is an integer from 1 to 10. X is particularly preferably bromine.

Most preferred are the aromatic halogen compounds of the formulae XI 1 to XI 24 shown below:

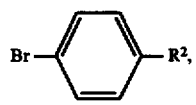   XI 1

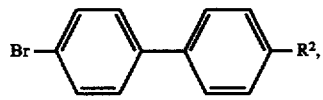   XI 2

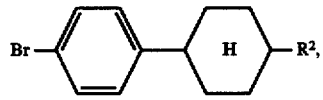   XI 3

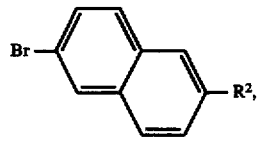   XI 4

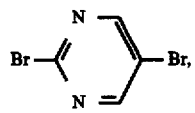   XI 5

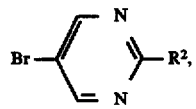   XI 6

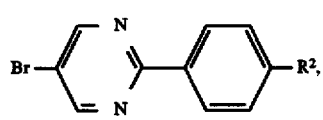   XI 7

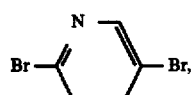   XI 8

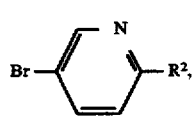   XI 9

-continued

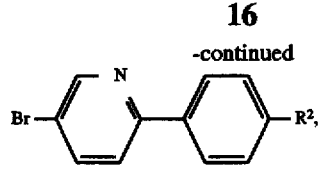   XI 10

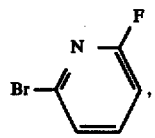   XI 11

   XI 12

   XI 13

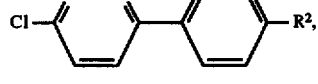   XI 14

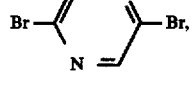   XI 15

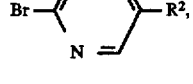   XI 16

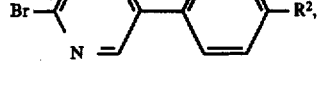   XI 17

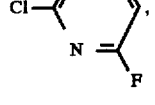   XI 18

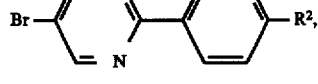   XI 19

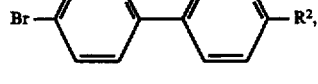   XI 20

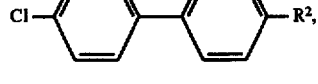   XI 21

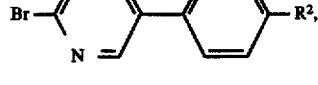   XI 22

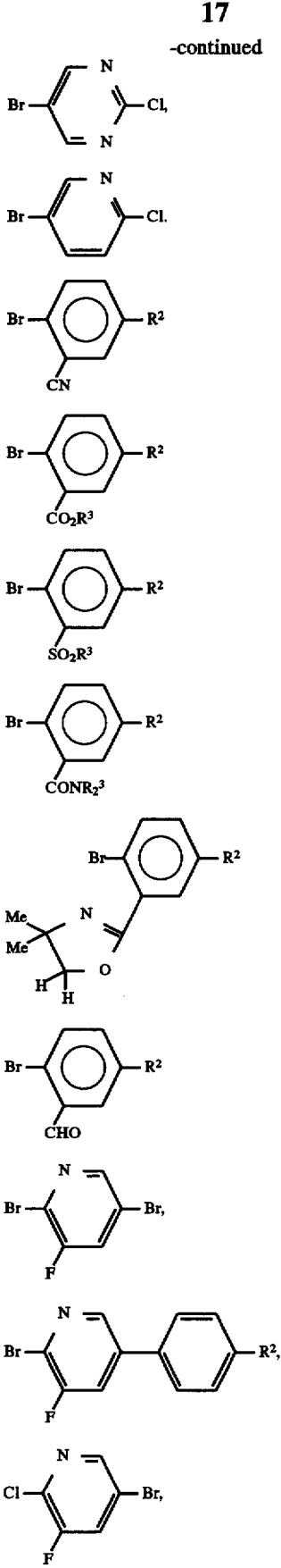

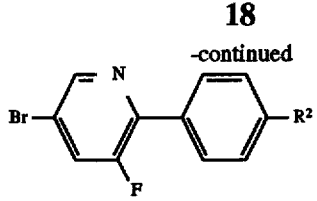

where $R^2$ and $R^3$ are each benzyloxy, H, methyl, ethyl, propyl, butyl, pentyl, hexyl, heptyl, octyl, nonyl, decyl, undecyl, dodecyl, tridecyl, tetradecyl and pentadecyl, and also methyloxy, ethyloxy, propyloxy, butyloxy, pentyloxy, hexyloxy, heptyloxy, octyloxy, nonyloxy, decyloxy, undecyloxy, dodecyloxy, tridecyloxy, tetradecyloxy and pentadecyloxy.

The aromatic halogen compounds and perfluoroalkylsulfonates used are either known or can be prepared by known methods as are described, for example, in Houben Weyl, Methoden der Organischen Chemie, Georg Thieme Verlag, Stuttgart, Volumes 5/3 and 5/4. For example, aromatic halides can be obtained by replacing the diazonium group of a corresponding diazonium salt by chlorine, bromine or iodine.

Furthermore, hydroxy-nitrogen heterocycles can be converted into the corresponding halides by means of phosphorus trihalides and phosphorus oxytrihalides. The process of the invention for cross-coupling aromatic boron compounds with aromatic halogen compounds or perfluoroalkylsulfonates can likewise be used for preparing compounds of the formula XI. Perfluoroalkylsulfonates of the formula III in which X is $OSO_2$—$C_nH_{2n+1}$ can be prepared by esterification of corresponding alcohols of the formula III, in which X is a hydroxyl group, with perfluoroalkanesulfonic acids or their reactive derivatives. The corresponding perfluoroalkanesulfonic acids are known. Suitable reactive derivatives of said perfluoroalkanesulfonic acids are, in particular, the acid halides, primarily the chlorides and bromides, also the anhydrides.

Products of the process of the invention are polycyclic aromatic compounds.

Preferred products formed in the process of the invention are compounds of the formula XII

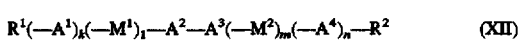
(XII)

where $R^1$ and $R^2$ can each be, independently of one another, benzyloxy, H, F, Cl, Br, —NC, —CN, —$CF_3$, —$OCF_3$ or a straight-chain or branched (with or without an asymmetric carbon atom) alkyl radical having from 1 to 18 carbon atoms, with one or two non-adjacent —$CH_2$— groups also being able to be replaced by —O—, —S—, —CO—, —CO—O—, —O—CO—, —CO—S—, —S—CO—, —O—CO—O—, —CH=CH—, —C≡C—, —$SO_2$—, —CON(H, $C_1$-$C_8$-alkyl)—,

or —$Si(CH_3)_2$—, and with one or more hydrogen atoms of the alkyl radical also being able to be replaced by F, Cl, Br or CN, $A^1$ and $A^4$ can each be, independently of one another, 1,4-phenylene, pyrazine-2,5-diyl, pyridazine-3,6-diyl, pyridine-2,5-diyl, pyrimidine-2,5-diyl, naphthalene-2,6-diyl, trans-1,4-cyclohexylene in which one or two non-adjacent $CH_2$ groups can be replaced by —O— or —S—, with one or more hydrogen atoms being able to be replaced by identical or different substituents L, with L having the meanings given for $R^1$ or being 4,4-dimethylisoxazoline, or can be 1,3,4-thiadiazole-2,5-diyl, 1,3-thiazole-2,4-diyl, 1,3-thiazole-2,5-diyl, thiophene-2,4-diyl, thiophene-2,5-diyl, piperazine-1,4-diyl, piperazine-2,5-diyl, piperidine-1,4-diyl, bicyclo[2.2.2]octane-1,4-diyl, 1,3-dioxaborinane-2,5-diyl or trans-decalin-2,6-diyl, $A^2$ and $A^3$ can each be, independently of one another, 1,4-phenylene, pyrazine-2,5-diyl, pyridazine-3,6-diyl, pyridine-2,5-diyl, pyrimidine-2,5-diyl, naphthalene-2,6-diyl, with one or more hydrogen atoms being able to be replaced by identical or different substituents L, with L having the meanings given for $R^1$ or being 4,4-dimethylisoxazoline or, in the case of $A^3$, also CHO, or can be 1,3,4-thiadiazole-2,5-diyl, 1,3-thiazole-2,4-diyl, 1,3-thiazole-2,5-diyl, thiophene-2,4-diyl or thiophene-2,5-diyl, $M^1$ and $M^2$ can each be, independently of one another, —O—, —S—, —CO—, —CO—O—, O—CO—, —CO—S, —S—CO—, —O—CO—O—, —CH$_2$—O—, —OCH$_2$—, —CH$_2$CH$_2$—, —CH=CH—, —C≡C—, —CH(CN)—CH$_2$—, —CH$_2$—CH(CN)—, —CH=N—, —N=CH—, —CH$_2$CH$_2$CH$_2$—O—, —OCH$_2$CH$_2$CH$_2$—, —CH$_2$CH$_2$CO—O—, —O—COCH$_2$CH$_2$—, and k, l, m, n are each, independently of one another, zero or one.

Preferred and particularly preferred variants of $R^1$, $R^2$, $A^1$, $A^2$, $A^3$, $A^4$, $M^1$, $M^2$, k, l, m, n are those given in the formulae II and III.

Most preferred are the compounds of the formulae XII 1 to XII 94 shown below:

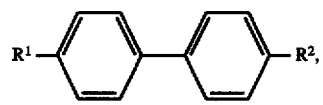 XII 1

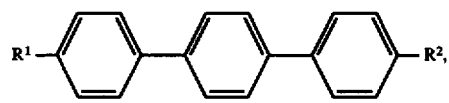 XII 2

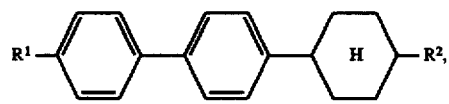 XII 3

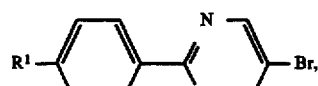 XII 4

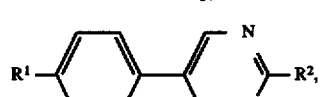 XII 5

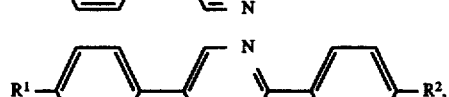 XII 6

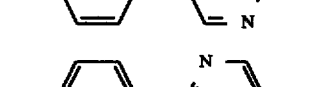 XII 7

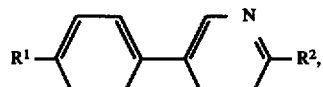 XII 8

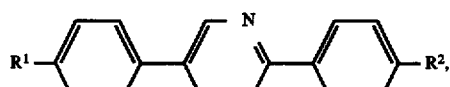 XII 9

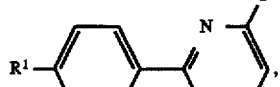 XII 10

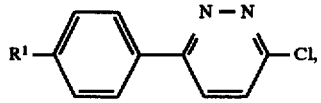 XII 11

 XII 12

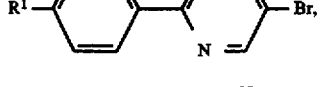 XII 13

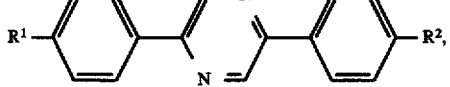 XII 14

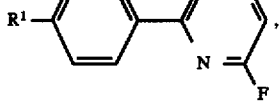 XII 15

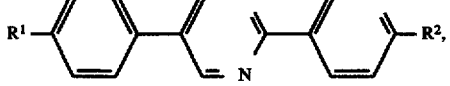 XII 16

 XII 17

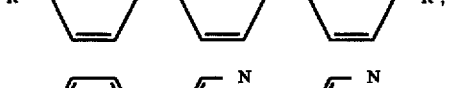 XII 18

 XII 19

 XII 20

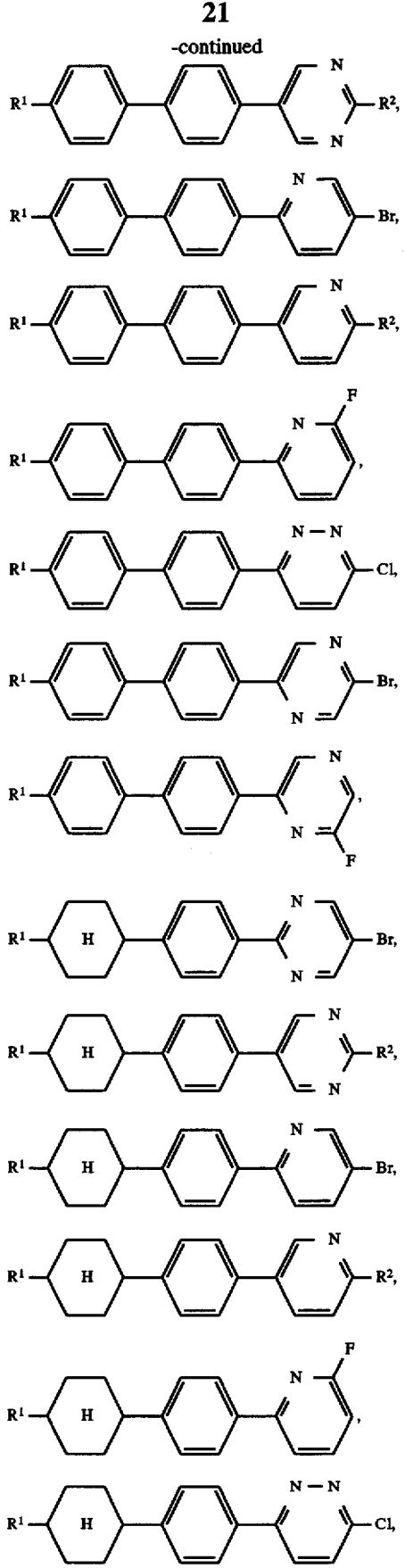
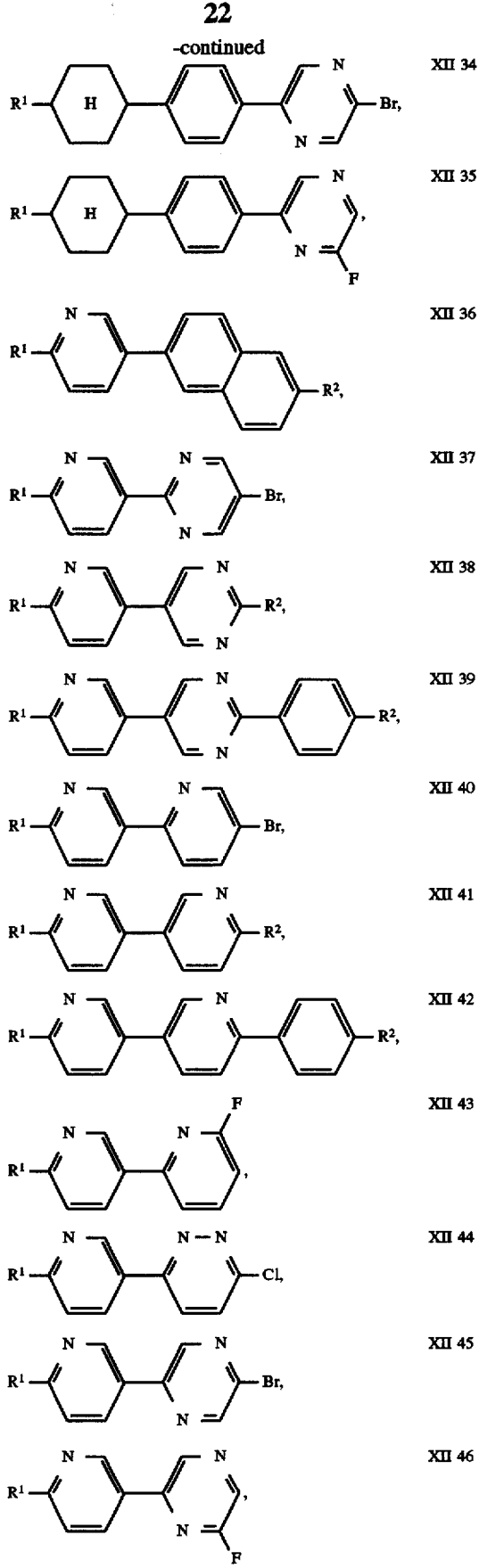

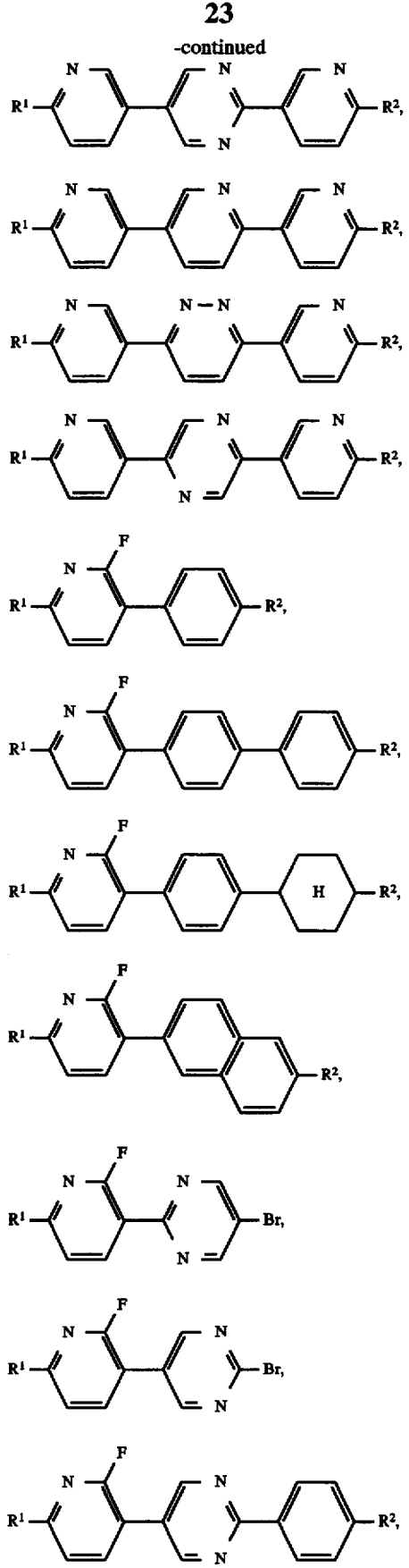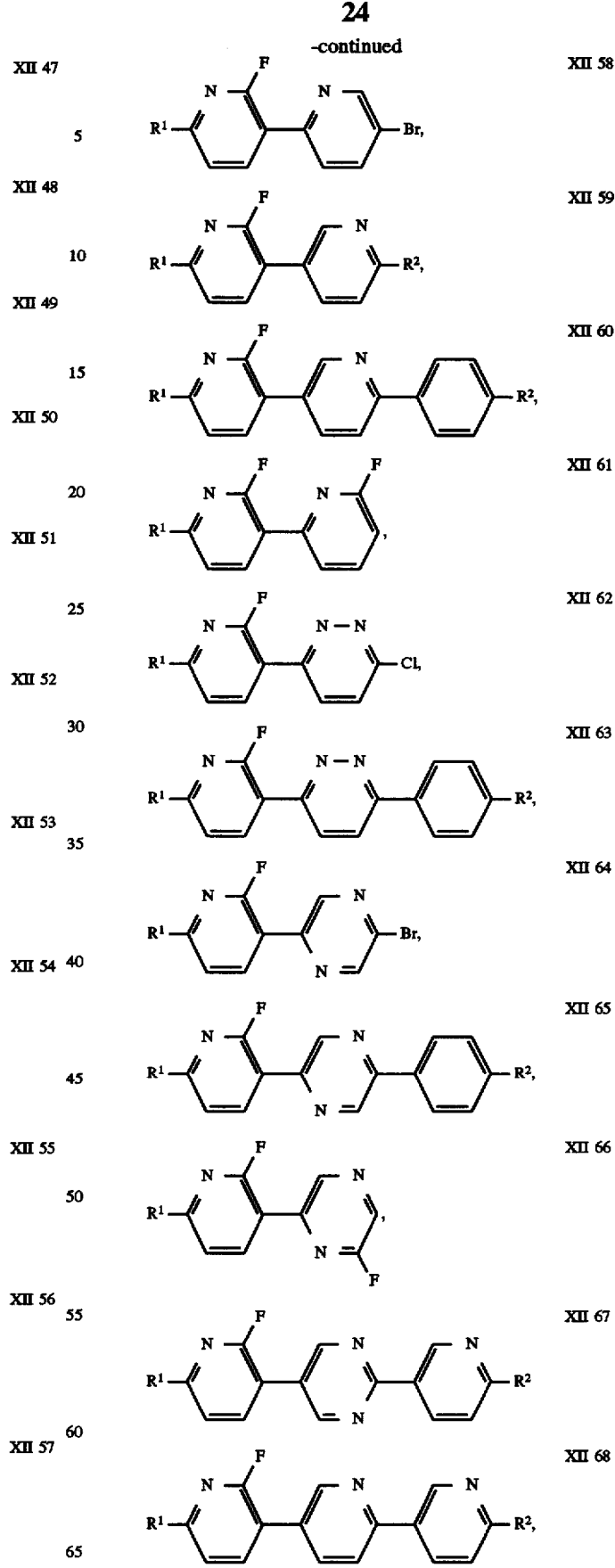

-continued
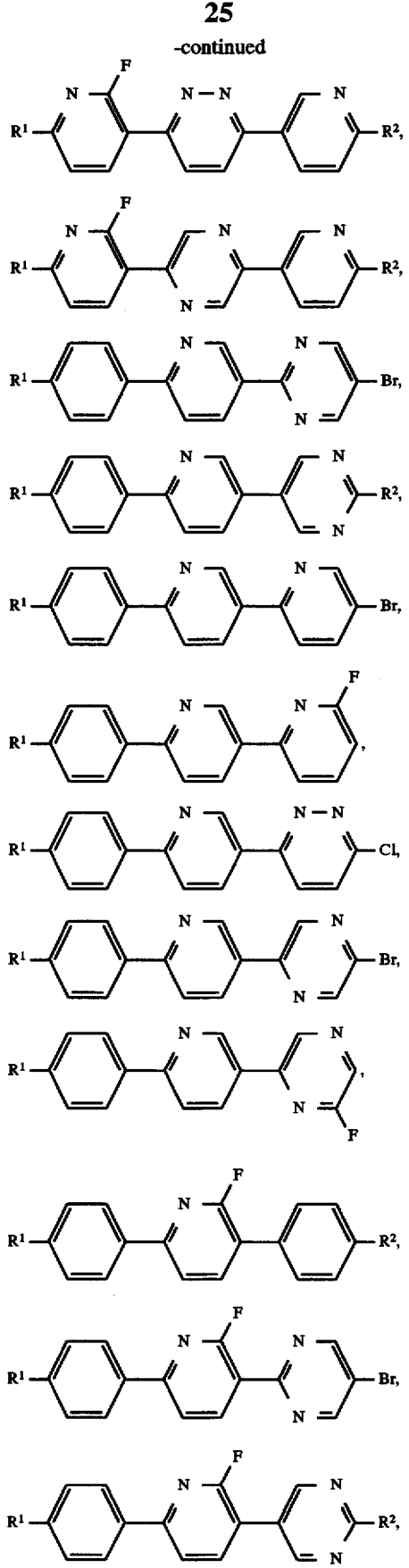
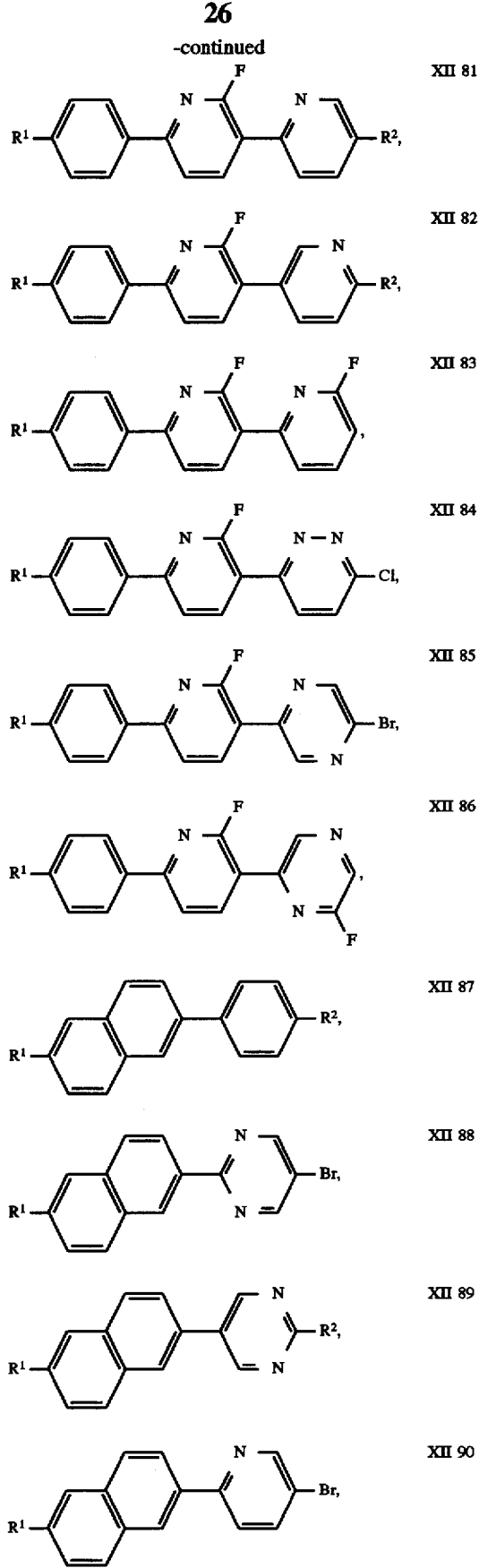

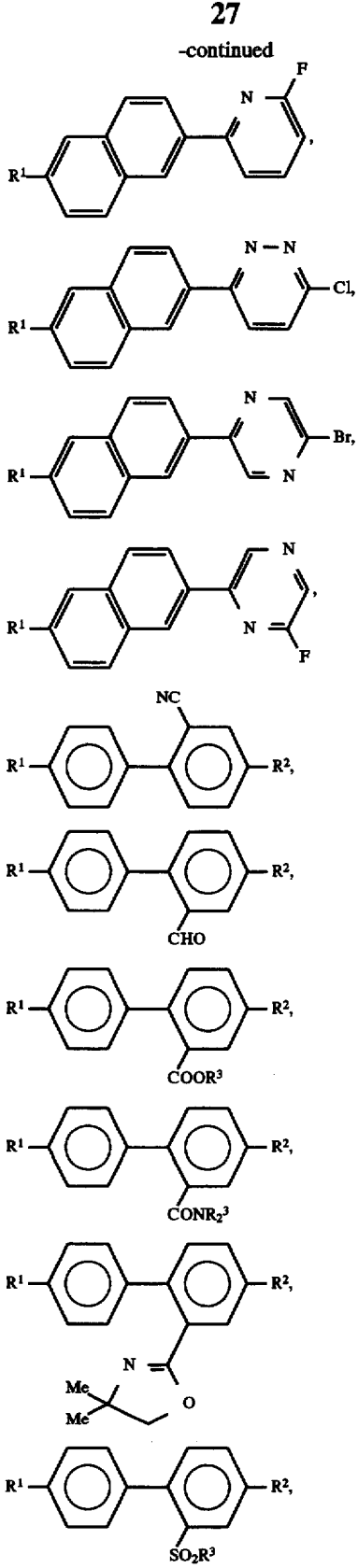

where $R^1$, $R^2$ and $R^3$ are each benzyloxy, H, methyl, ethyl, propyl, butyl, pentyl, hexyl, heptyl, octyl, nonyl, decyl, undecyl, dodecyl, tridecyl, tetradecyl and pentadecyl, and also methoxy, ethoxy, propoxy, butoxy, pentoxy, hexoxy, heptoxy, octoxy, nonoxy, decoxy, undecoxy, dodecoxy, tridecoxy, tetradecoxy and pentadecoxy.

The compounds of the formula XII are suitable for use as liquid-crystalline materials, or can be used as intermediates for the preparation of further liquid-crystalline compounds. Furthermore, compounds of the formula I are used as precursors for pharmaceuticals, cosmetics, fungicides, herbicides, insecticides, dyes, detergents and polymers, including as additives in the same.

Compounds prepared according to the invention as are given, for example, by the formulae XII 95 to XII 100 are, in particular, valuable precursors for the angiotensin II inhibitors (see, for example, WO-A 89/12 1201).

The present invention is illustrated by the examples described below, without being limited thereby. The abbreviations used have the following meanings:

mp.=melting point
X=crystalline
S=smectic
$S_C$=smectic C
$S_A$=smectic A
N=nematic
I=isotropic

Example 1

2-Bromobenzonitrile (3.1 g) and 2.75 g of 4-methylphenylboronic acid are dissolved in 20 ml of toluene and 10 ml of ethanol. The solution is admixed with 0.18 g (1 mol %) of palladium on activated carbon (10% by weight) and 4.47 g of sodium carbonate in 10 ml of water. 0.36 mmol of trisodium triphenylphosphine-3,3',3"-trisulfonate (TTPTS) is subsequently added. The mixture is heated at 80° C. for 12 hours. After the reaction is complete, the mixture is cooled to room temperature and the organic phase is separated off. The aqueous phase is extracted three times by shaking with dichloromethane. The combined organic phases are dried over magnesium sulfate and the solvents are subsequently evaporated on a rotary evaporator. The residue is crystallized from 50 ml of n-heptane (2.9 g of 4-methyl-2'-cyanobiphenyl). Melting point 49° C.

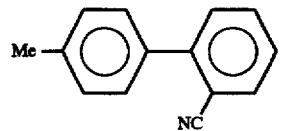

Example 2

2-Bromobenzonitrile (3.1 g) and 2.75 g of 4-methylphenylboronic acid are dissolved in 20 ml of toluene and 10 ml of ethanol. The solution is admixed with 0.018 g (0.1 mol %) of palladium on activated carbon (10% by weight) and 4.47 g of sodium carbonate in 10 ml of water. 0.036 mmol of trisodium triphenylphosphine-3,3',3"-trisulfonate (TTPTS) is subsequently added. The mixture is heated at 80° C. for 18 hours. After the reaction is complete, the mixture is cooled to room temperature and the organic phase is separated off. The aqueous phase is extracted three times by shaking with dichloromethane. The combined organic phases are dried over magnesium sulfate and the solvents are subsequently evaporated on a rotary evaporator. The residue is crystallized from 50 ml of n-heptane (2.7 g of 4-methyl-2'-cyanobiphenyl).

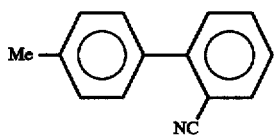

Example 3

2-Bromobenzonitrile (3.1 g) and 2.75 g of 4-methylphenylboronic acid are dissolved in 20 ml of toluene and 10 ml of ethanol. The solution is admixed with 0.18 g (1 mol %) of palladium on activated carbon (10% by weight) and 4.47 g of sodium carbonate in 10 ml of water. 0.18 mmol of BINAS is subsequently added. The mixture is heated at 80° C. for 12 hours. After the reaction is complete, the mixture is cooled to room temperature and the organic phase is separated off. The aqueous phase is extracted three times by shaking with dichloromethane. The combined organic phases are dried over magnesium sulfate and the solvents are subsequently evaporated on a rotary evaporator. The residue is crystallized from 50 ml of n-heptane (2.55 g of 4-methyl-2'-cyanobiphenyl).

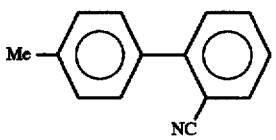

Example 4

2-Bromobenzonitrile (3.1 g) and 2.75 g of 4-methylphenylboronic acid are dissolved in 20 ml of toluene and 10 ml of ethanol. The solution is admixed with 0.018 g (0.1 mol %) of palladium on activated carbon (10% by weight) and 4.47 g of sodium carbonate in 10 ml of water. 0.018 mmol of BINAS is subsequently added. The mixture is heated at 80° C. for 12 hours. After the reaction is complete, the mixture is cooled to room temperature and the organic phase is separated off. The aqueous phase is extracted three times by shaking with dichloromethane. The combined organic phases are dried over magnesium sulfate and the solvents are subsequently evaporated on a rotary evaporator. The residue is crystallized from 50 ml of n-heptane (2.45 g of 4-methyl-2'-cyanobiphenyl).

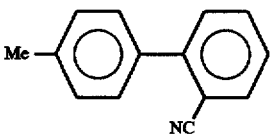

Example 5

2-Bromobenzonitrile (25.77 g) and 22.86 g of 4-methylphenylboronic acid are dissolved in 166 ml of toluene and 83 ml of ethanol. The solution is admixed with 0.15 g (0.1 mol %) of palladium on activated carbon (10% by weight) and 37.16 g of sodium carbonate in 83 ml of water. 2.83 mmol of TPPTS are subsequently added. The mixture is heated at 80° C. for 18 hours. After the reaction is complete, the mixture is cooled to room temperature and the organic phase is separated off. The aqueous phase is extracted three times by shaking with dichloromethane. The combined organic phases are dried over magnesium sulfate and the solvents are subsequently evaporated on a rotary evaporator. The residue is crystallized from 500 ml of n-heptane (24.5 g of 4-methyl-2'-cyanobiphenyl).

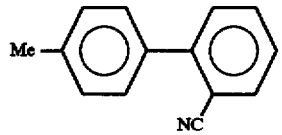

Example 6

10.43 g (0.044 mol) of 2,5-dibromopyrimidine, 10 g (0.044 mol) of 4-(phenylmethoxy)benzeneboronic acid, 0.475 g (0.00044 mol) of palladium on activated carbon (10% by weight), (0.001752 mol) of TPPTS and 9.3 g (0.0876 mol) of sodium carbonate are heated in 100 ml of toluene, 50 ml of ethanol and 30 ml of water at 80° C. for 48 hours. The palladium catalyst is subsequently separated from the reaction mixture at 80° C. by filtration. The aqueous lower phase of the reaction mixture is separated off at 80° C. before the organic phase is freed of the solvents on a rotary evaporator and is dried in a high vacuum. The crude product thus obtained is crystallized from acetonitrile (300 ml), giving 14.5 g (93% yield, based on 2,5-dibromopyrimidine) of 5-bromo-2-[4-(phenylmethoxy)phenyl]pyrimidine (content according to HPLC: 98%).

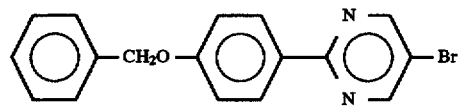

Example 7

The procedure of Example 6 is repeated using 27.7 g (100 mmol) of 5-[1,3,2]dioxaborolan-2-yl-2-octyloxypyridine and 28.9 g (100 mmol) of 5-bromo-2-octyloxypyrimidine, 0.53 g (0.5 mmol) of palladium on activated carbon, 2 mmol of BINAS and 21.2 g (200 mmol) of sodium carbonate. After chromatography on silica gel, this gives 39.7 g (96%) of product.

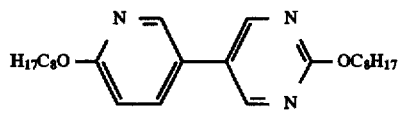

Phase order: X 64 $S_C$ 67 $S_A$ 91 I

Example 8

The procedure of Example 6 is repeated using 24.3 g (100 mmol) of 2-bromo-5-hexylpyrimidine and 21.9 g (100 mmol) of 4-hexyloxybenzeneboronic acid, 0.53 g (0.5 mmol) of palladium on activated carbon, 2 mmol of BINAS and 21.2 g (200 mmol) of sodium carbonate. After chromatography on silica gel, this gives 32.3 g (95%) of product.

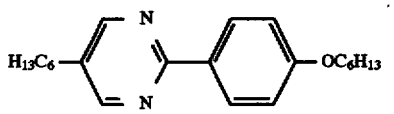

Phase order: X₁ 15 X₂ 32 N 61 I

Example 9

2-Bromobenzonitrile (3.1 g) and 3.9 g of p-(benzyloxy)-phenylboronic acid are dissolved in 20 ml of toluene and 10 ml of ethanol. The solution is admixed with 0.18 g (1 mol %) of palladium on activated carbon (10% by weight) and 4.47 g of sodium carbonate in 10 ml of water. 0.36 mmol of TPPTS is subsequently added. The mixture is heated at 80° C. for 12 hours. After the reaction is complete, the mixture is cooled to room temperature and the organic phase is separated off. The aqueous phase is extracted three times by shaking with dichloromethane. The combined organic phases are dried over magnesium sulfate and the solvents are subsequently evaporated on a rotary evaporator. The residue is crystallized from 50 ml of n-heptane (4.36 g of (benzyloxy)-2'-cyanobiphenyl).

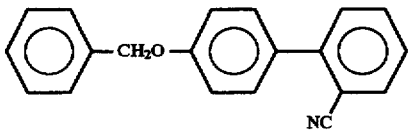

Example 10

2-Bromobenzonitrile (3.1 g) and 3.9 g of p-(benzyloxy)-phenylboronic acid are dissolved in 20 ml of toluene and 10 ml of ethanol. The solution is admixed with 0.18 g (1 mol %) of palladium on activated carbon (10% by weight) and 4.47 g of sodium carbonate in 10 ml of water. 0.18 mmol of BINAS is subsequently added. The mixture is heated at 80° C. for 12 hours. After the reaction is complete, the mixture is cooled to room temperature and the organic phase is separated off. The aqueous phase is extracted three times by shaking with dichloromethane. The combined organic phases are dried over magnesium sulfate and the solvents are subsequently evaporated on a rotary evaporator. The residue is crystallized from 50 ml of n-heptane (4.3 g of 4-(benzyloxy)-2'-cyanobiphenyl).

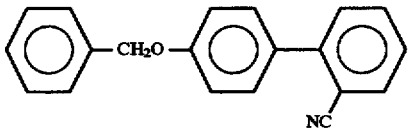

We claim:

1. A process for preparing polycyclic aromatic compounds by cross-coupling aromatic boron compounds with aromatic halogen compounds or perfluoroalkylsulfonates in the presence of a base and of metallic palladium as catalyst, which comprises adding to the reaction
   (a) at least one water-soluble complexing ligand selected from the group consisting of phosphanes, phosphites, phosphonous esters, phosphinous esters, phospholes, bipyridines, phenanthrolines, porphyrines and alizarins, and
   (b) sufficient water for the reaction mixture to form an aqueous phase.

2. The process as claimed in claim 1, wherein a polycyclic aromatic compound of the formula XII $$R^1(-A^1)_k(-M^1)_l-A^2-A^3(-M^2)_m(-A^4)_n-R^2 \quad (XII)$$

where $R^1$ and $R^2$ can each be, independently of one another, benzyloxy, H, F, Cl, Br, —NC, —CN, —CF₃, —OCF₃ or a straight-chain or branched (with or without an asymmetric carbon atom) alkyl radical having from 1 to 18 carbon atoms, with one or two non-adjacent —CH₂— groups also being able to be replaced by —O—, —S—, —CO—, —CO—O—, —O—CO—, —CO—S—, —S—CO—, —O—CO—O—, —CH=CH—, —C≡C—, —SO₂—, —CON(H, C₁-C₈-alkyl)—,

or —Si(CH₃)₂—, and with one or more hydrogen atoms of the alkyl radical also being able to be replaced by F, Cl, Br or CN, $A^1$ and $A^4$ can each be, independently of one another, 1,4-phenylene, pyrazine-2,5-diyl, pyridazine-3,6-diyl, pyridine-2,5-diyl, pyrimidine-2,5-diyl, naphthalene-2,6-diyl, trans-1,4-cyclohexylene in which one or two non-adjacent CH₂ groups can be replaced by —O— or —S—, with one or more hydrogen atoms being able to be replaced by identical or different substituents L, with L having the meanings given for $R^1$ or being 4,4-dimethylisoxazoline, or can be 1,3,4-thiadiazole-2,5-diyl, 1,3-thiazole-2,4-diyl, 1,3-thiazole-2,5-diyl, thiophene-2,4-diyl, thiophene-2,5-diyl, piperazine-1,4-diyl, piperazine-2,5-diyl, piperidine-1,4-diyl, bicyclo[2.2.2]octane-1,4-diyl, 1,3-dioxaborinane-2,5-diyl or trans-decalin-2,6-diyl, $A^2$ and $A^3$ can each be, independently of one another, 1,4-phenylene, pyrazine-2,5-diyl, pyridazine-3,6-diyl, pyridine-2,5-diyl, pyrimidine-2,5-diyl, naphthalene-2,6-diyl, with one or more hydrogen atoms being able to be replaced by identical or different substituents L, with L having the meanings given for $R^1$, or being 4,4-dimethylisoxazoline or, in the case of $A^3$, also CHO, or can be 1,3,4-thiadiazole-2,5-diyl, 1,3-thiazole-2,4-diyl, 1,3-thiazole-2,5-diyl, thiophene-2,4-diyl or thiophene-2,5-diyl, $M^1$ and $M^2$ can each be, independently of one another, —O—, —S—, —CO—, —CO—O—, O—CO—, —CO—S, —S—CO—, —O—CO—O—, —CH₂—O—, —OCH₂—, —CH₂CH₂—, —CH=CH—, —C≡C—, —CH(CN)—CH₂—, —CH₂—CH(CN)—, —CH=N—, —N=CH—, —CH₂CH₂CH₂—O—, —OCH₂CH₂CH₂—, —CH₂CH₂CO—O—, —O—COCH₂CH₂—, k, l, m, n are each, independently of one another, zero or one, is prepared by reacting an aromatic boron compound of the formula (VII)

$$R^1(-A^1)_k(-M^1)_l-A^2-BQ_1Q_2 \quad (VII)$$

where $R^1$, $A^1$, $A^2$, $M^1$, k and l have the meanings given above, $Q_1,Q_2$ are identical or different and are each —OH, C₁-C₄-alkoxy, C₁-C₄-alkyl, phenyl which can be unsubstituted or substituted by C₁-C₄-alkyl, C₁-C₄-alkoxy or halogen, or halogen or $Q_1$ and $Q_2$ together form a $C_1$–$C_4$-alkylenedioxy group, a methylene group which can be unsubstituted or substituted by one or two $C_1$–$C_4$-alkyl groups or $Q_1$ and $Q_2$ and the boron atom are together part of a boroxine ring of the formula (IX):

(IX)

with a compound of the formula (XI)

$$X\text{—}A^3(\text{—}M^2)_m(\text{—}A^4)_n\text{—}R^2 \qquad (XI),$$

where $R^2$, $R^3$, $A^3$, $A^4$, $M^2$, m and n have the meanings given above, and X is chlorine, bromine, iodine or $OSO_2\text{—}C_pF_{2p+1}$, where p is an integer from 1 to 10.

3. The process as claimed in claim 1, wherein the water-soluble ligand is added in a proportion of 0.1–20 mol %, based on the aromatic halogen compound or the aromatic perfluoroalkylsulfonate.

4. The process as claimed in claim 1, wherein the base used is at least one compound selected from the group consisting of alkali metal and alkaline earth metal hydroxides, alkali metal and alkaline earth metal carbonates, alkali metal hydrogen carbonates, alkali metal and alkaline earth metal acetates, alkali metal and alkaline earth metal alkoxides and primary, secondary and tertiary amines.

5. The process as claimed in claim 4, wherein the base is used in a proportion of 100–500 mol %, based on the aromatic boronic acid.

6. The process as claimed in claim 1, carried out at temperatures between 50° and 150° C.

7. The process as claimed in claim 1, wherein the cross-coupling reaction is carried out in a solvent mixture containing water and at least one compound selected from the group consisting of ethers, hydrocarbons, alcohols, ketones, amides and nitriles.

8. The process as claimed in claim 1, wherein the catalyst used is palladium in pulverized form, palladium on activated carbon, palladium on aluminum oxide, palladium on barium sulfate or palladium on calcium carbonate, in each case having a palladium content of from 0.5 to 10% by weight.

9. The process as claimed in claim 1, wherein components of liquid crystal mixtures or intermediates in the synthesis of components for liquid crystal mixtures are prepared.

10. The process as claimed in claim 1, wherein an intermediate in the synthesis of an angiotensin II inhibitor is prepared.

* * * * *